United States Patent
Maguire et al.

[11] Patent Number: 5,913,854
[45] Date of Patent: Jun. 22, 1999

[54] FLUID COOLED ABLATION CATHETER AND METHOD FOR MAKING

[75] Inventors: Mark A. Maguire, San Jose; Hong Li, Cupertino; Joseph M. Karratt, Sunnyvale; Aurelio Valencia, East Palo Alto, all of Calif.

[73] Assignee: Medtronic, Inc., Minneapolis, Mich.

[21] Appl. No.: 08/794,803

[22] Filed: Feb. 4, 1997

[51] Int. Cl.⁶ ........................................ A61N 1/05
[52] U.S. Cl. ............................... 606/41; 607/122
[58] Field of Search ................... 606/27, 28, 29, 606/32, 33, 41, 46; 600/373, 374, 381; 607/119, 122

[56] References Cited

U.S. PATENT DOCUMENTS

| | | |
|---|---|---|
| 5,246,438 | 9/1993 | Langberg . |
| 5,334,193 | 8/1994 | Nardella . |
| 5,348,554 | 9/1994 | Imran et al. . |
| 5,383,876 | 1/1995 | Nardella ................................ 606/49 |
| 5,423,807 | 6/1995 | Milder . |
| 5,423,811 | 6/1995 | Imran et al. . |
| 5,431,648 | 7/1995 | Lev . |
| 5,462,521 | 10/1995 | Brucker et al. . |
| 5,487,757 | 1/1996 | Truckai et al. . |
| 5,545,161 | 8/1996 | Imran ..................................... 606/41 |
| 5,607,422 | 3/1997 | Smeets et al. ......................... 606/41 |
| 5,643,197 | 7/1997 | Brucker et al. ........................ 606/46 |
| 5,687,723 | 11/1997 | Avitall .................................... 606/41 |
| 5,688,267 | 11/1997 | Panescu et al. ........................ 606/42 |
| 5,697,928 | 12/1997 | Walcott et al. ......................... 606/41 |

FOREIGN PATENT DOCUMENTS

| | | |
|---|---|---|
| 0608 609 A2 | 8/1994 | European Pat. Off. . |
| 96/39966 | 12/1996 | WIPO . |

*Primary Examiner*—Jeffrey R. Jastrzab
*Assistant Examiner*—David M. Ruddy
*Attorney, Agent, or Firm*—Townsend and Townsend and Crew LLP

[57] ABSTRACT

A catheter assembly (2) includes a catheter shaft (6) having a tip portion (10) with a hollow interior (30) and a linear ablation electrode (18, 34, 36, 44, 58) spaced apart from the distal end (22) of the tip portion. The electrode has an inner surface (28) which is effectively fluidly exposed to the hollow interior so that a cooling fluid (32) passing through the interior contacts the inner surface so to effectively cool the electrode. The electrode can include a series of band electrodes (18, 34) or one or more spiral electrodes (36, 44, 58). One method for making the tip portion involves mounting the electrode to a mandrel, filling the spaces between the edges (26) of the electrode with a polymer and then removing the resulting tubular structure from the mandrel. The cooling fluid can pass through a hollow spiral electrode (58) for enhanced cooling effectiveness.

26 Claims, 6 Drawing Sheets

FLUID COOLED ABLATION CATHETER AND METHOD FOR MAKING

CROSS-REFERENCE TO RELATED APPLICATIONS

This application is related to U.S. patent application Ser. No. 08/794,840, entitled "Systems and Methods for Tissue Mapping and Ablation," (Attorney Docket 14875-002700), and U.S. patent application Ser. No. 08/794,066, entitled "Linear Ablation Catheter," (Attorney Docket 14875-003100), both filed on the same day as this application and both assigned to the same assignee, the disclosures of which are incorporated by reference.

BACKGROUND OF THE INVENTION

Catheter assemblies are often used to ablate surface tissue within a heart. The catheter assembly typically includes a handle and a catheter shaft extending from the handle, the catheter shaft having a tip portion. The tip portion typically includes a tip ablation electrode at the distal end and a linear ablation electrode along the tip portion spaced apart from the tip electrode. The linear ablation electrode is typically a series of circular band electrodes, one or more spiral electrodes or one or more braided electrodes. While it is desirable to ablate tissue at the target site, it is not desirable to overheat the tissue, or the blood in the vicinity of a target site, because blood can desiccate causing coagulum.

SUMMARY OF THE INVENTION

The present invention is directed to an ablation catheter assembly in which one or more linear ablation electrodes extending along the catheter shaft are cooled by permitting cooling fluid, typically saline, to effectively directly contact the inner surface of the linear ablation electrodes.

The fluid cooled ablation catheter assembly includes a catheter shaft having a tip portion with a hollow interior, defining a fluid passage, and a distal end. The tip portion also has a linear ablation electrode spaced apart from the distal end. The linear electrode has an inner surface which is effectively fluidly exposed to the fluid passage of the tip portion so that a cooling fluid passing through the fluid passage effectively directly contacts the inner surface so to efficiently cool the linear electrode. A primary advantage of the invention is that it permits electrodes at other than the tip of the catheter to be efficiently cooled using a cooling fluid.

The inner surface of the linear electrode is effectively fluidly exposed to the cooling fluid in two basic ways. First, the inner surface of the linear electrode can be an uncoated, bare surface so the cooling fluid wets the bare surface. This can occur by having all or part of the inner surface directly or indirectly fluidly coupled to the fluid passage of the tip portion. It can also occur if all or part of the inner surface of the linear electrode is covered by a porous material which allows the cooling fluid to contact the bare inner surface of the linear electrode. Second, the inner surface can be covered by a material which prevents direct contact by the cooling fluid with a bare inner surface of the linear electrode; in this event the material must be such to not impede heat transfer between the inner surface of the linear electrode and the cooling fluid to any significant extent. Such a material would preferably have a thermal conductivity adequate to allow the cooling fluid to maintain an electrode temperature between about body temperature (37° C.), or slightly below, and 100° C., but more preferably between about 37° C. and 70° C. to reduce the risk of blood coagulation. Such a covering material may be desired or necessary to ensure the columnar integrity of the catheter shaft is maintained even though a less-than-optimal bond is typically created between the metal electrode and the shaft. For example, a thin layer of PTFE, polyamide or PET, such as 0.0005"–0.002" thick, could be used to cover the inner surface of the linear electrode and catheter shaft and not significantly impede heat transfer between the cooling fluid and the linear electrode. Although these materials may not be good heat conductors, the thinness of the layer in this example keeps its thermal insulation properties to a reasonably low value. Therefore, the cooling fluid is considered to effectively directly contact the inner surface of the linear ablation electrode when the heat transfer from the linear electrode to the cooling fluid is such that the electrode temperature is maintained at the temperatures discussed above.

One method for making the tip portion of the catheter shaft involves mounting the electrodes to a mandrel and then filling the spaces between the edges of the electrodes with a polymer. Other assembly and construction methods can also be used.

The cooling fluid can be directed out of the catheter at the distal end of the tip portion. Cooling fluid can also be directed out of the catheter (into the bloodstream) at locations other than the distal end. For example, exit holes for fluid egress can be located on or between individual ablation electrodes.

Alternatively, the cooling fluid can be partly or totally recirculated, that is directed back up through the catheter shaft after having passed and cooled the linear electrode. Therefore, the amount of cooling is not limited by the amount of the cooling fluid, such as saline, that can be properly or safely injected into the patient. This recirculation ability is therefore useful when it is desirable to limit or prevent injection of fluid into the patient.

Other features and advantages of the invention will appear from the following description in which the preferred embodiments have been set forth in detail in conjunction with the accompanying drawings.

DESCRIPTION OF THE PREFERRED EMBODIMENTS

Figure 1:
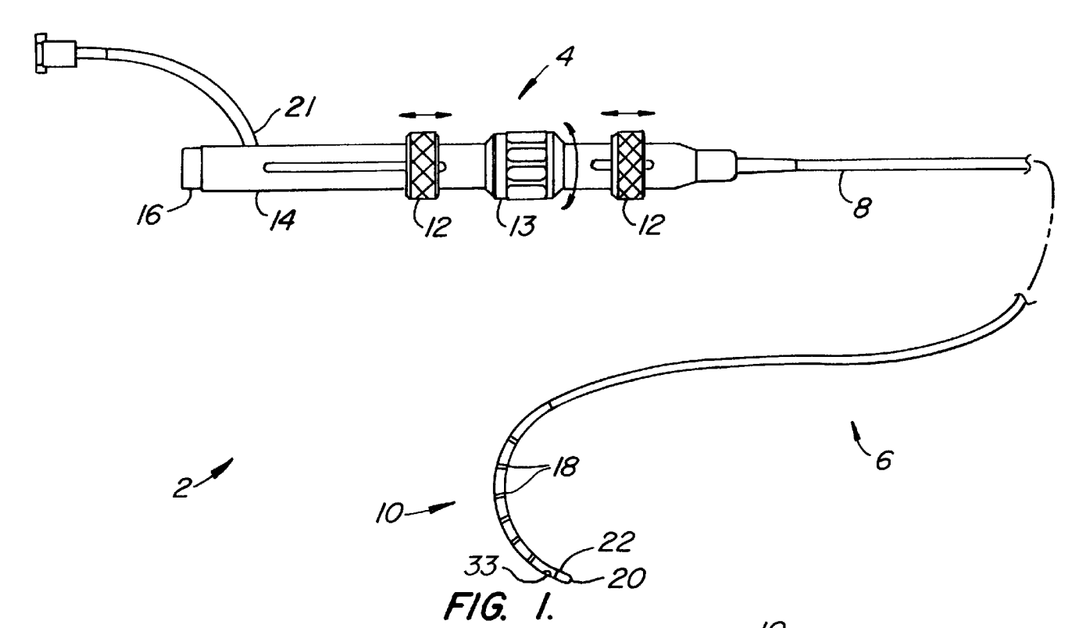
FIG. 1 is a simplified overall view of a catheter assembly made according to the invention.

FIG. 1 illustrates a catheter assembly 2 comprising a handle 4 and a catheter shaft 6 extending from the handle. Catheter shaft 6 includes a main portion 8 and tip portion 10. Tip portion 10 is, as is standard, relatively flexible to be maneuverable and placeable in different configurations by one or more manipulators 12, 13 mounted to body 14 of handle 4. Handle 4 includes an electrical connector 16 to permit electrical connection with a set of electrodes 18 carried by tip portion 10. Electrodes 18 are ablation-capable electrodes. Electrodes 18 are used to create linear lesions and are sometimes collectively referred to herein as a linear ablation electrode or a linear electrode. These various components discussed above with reference to FIG. 1 are generally conventional. See, for example, U.S. Pat. No. 5,487,757, entitled "Multicurved Deflectable Catheter" and U.S. patent application Ser. No. 08/613,298, filed Mar. 11, 1996, entitled "Method and Apparatus for RF Ablation", the disclosures of which are incorporated by reference. Handle 4 also has a fluid port 21 which permits saline, or another cooling fluid, to be directed through catheter shaft 6 to cool electrodes 18 as discussed below.

FIGS. 2–6 are simplified views and do not show various elements, such as radial deflection manipulator wires, lateral deflection core wires, thermocouple wires, electrical power wires, etc., for ease of illustration.

Figure 2:
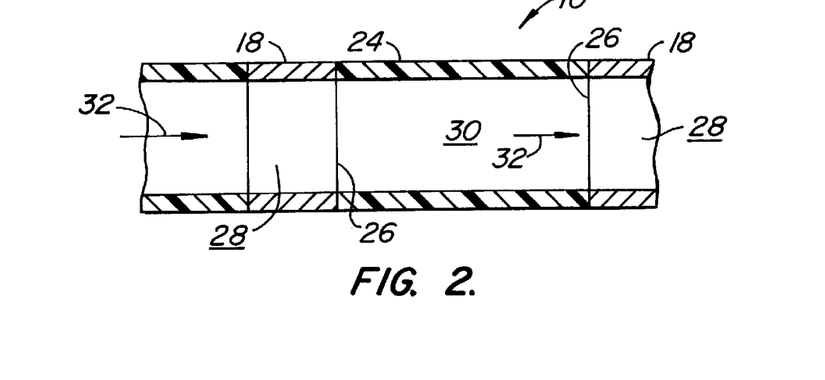
FIG. 2 is an enlarged, simplified cross-sectional view of a section of the tip portion of the catheter assembly of FIG. 1 using a series of circumferential band electrodes along the tip portion, the band electrodes spaced apart from the distal end of the tip portion.

FIG. 2 illustrates an enlarged simplified sectional view of a section of tip portion 10 including two band electrodes 18. Tip portion 10 is seen to include alternating lengths of band electrodes 18 and polymer sections 24 made of polyurethane or other suitable materials. Electrodes 18 of the embodiment of FIG. 2 may have the smooth sides indicated only if a sufficiently strong bond can be created between metal electrodes 18 and polymer sections 24. It may, however, be necessary to provide mechanical interlocking features which enhance the connection between electrodes 18 and sections 24.

Band electrodes 18 are typically made of platinum-iridium or stainless steel. In this way the inside surfaces 28 of band electrodes 18 are fully exposed to the interior 30 of tip portion 10. The provision of cooling fluid 32, typically saline, along interior 30 allows the cooling fluid to directly contact inside surface 28 of band electrodes 18 thus efficiently cooling the band electrodes during ablation procedures. Cooling fluid 32 passes through interior 30 and out an exit opening 33 adjacent to tip portion 10.

Figure 3:
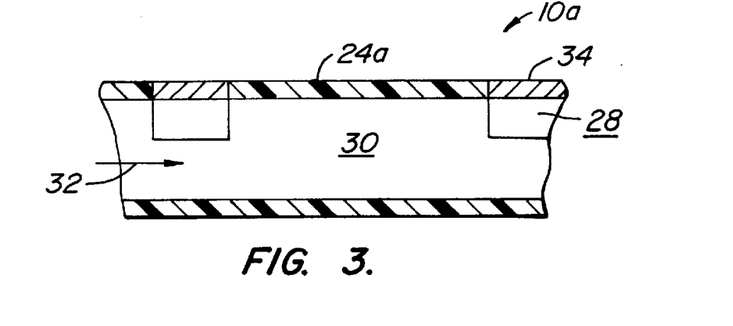
FIG. 3 is a view similar to FIG. 2 but using semicircular electrodes.

FIG. 3 illustrates an alternative embodiment of the invention similar to FIG. 2. However, instead of circumferential band electrodes 18, semicircular band electrodes 34 are used as the linear ablation electrode with tip portion 10a. This is to allow more cross-sectional area to be comprised of catheter shaft material to maintain adequate structural support.

Figure 4:
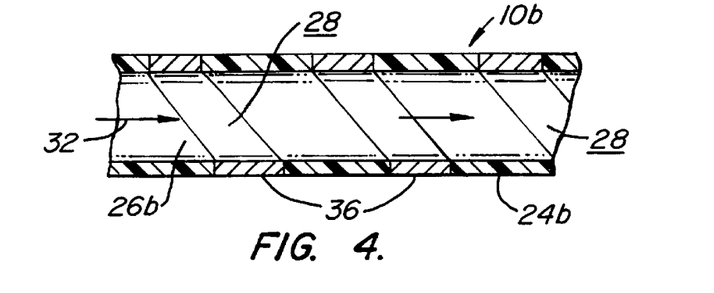
FIG. 4 is a view similar to FIG. 2 but using a spiral electrode.

FIG. 4 is an embodiment similar to FIG. 2 and shows a tip portion 10b using one or more spiral electrodes 36 as the linear ablation electrode.

Figure 5:
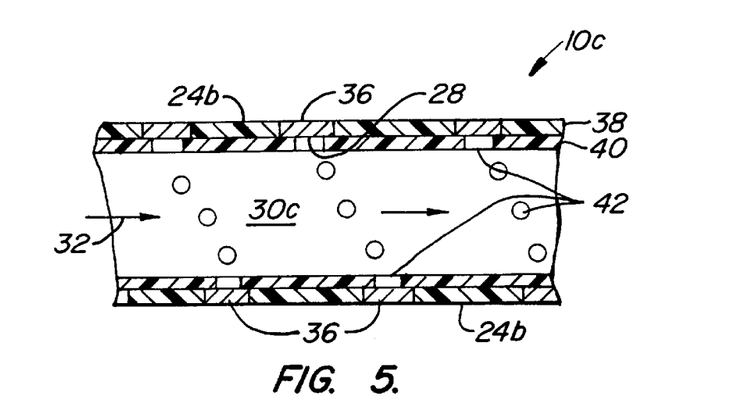
FIG. 5 shows a tip portion including an outer tubular member similar to the tip portion of FIG. 4 and an inner tubular member with a series of holes providing fluid access to the inside surface of the spiral electrode.

FIG. 5 illustrates a tip portion 10c comprising an outer tubular member 38 similar in construction to tip portion 10b and an inner tubular member 40. Inner tubular member 40 is made of a polymer material, such as polyurethane, silicone, PET or polyimide, and has a series of holes 42 therein. Holes 42 are positioned to be aligned with the inner surface 28 of spiral electrodes 36. In this way the interior 30c of tip portion 10c is in fluid communication with the inside surface 28 of spiral electrodes 36 to permit cooling saline 32 to contact inner surface 28 of spiral electrodes 36.

Inner tubular member 40 could be replaced by a braided tubular structure to provide uniform shaft support for the electrodes; such a braided or other woven tubular structure would have numerous and substantial openings so the cooling fluid can contact the inside surfaces of the electrodes.

Figure 6:
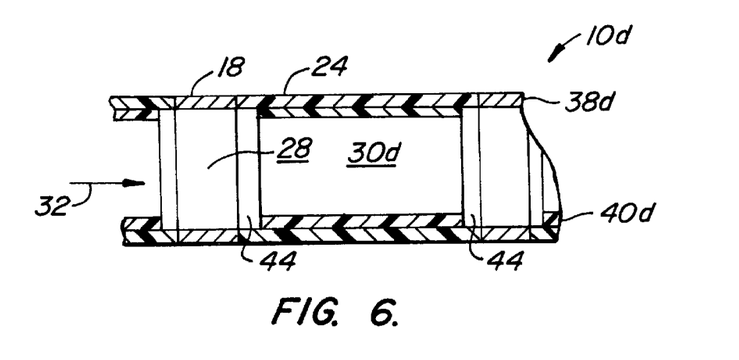
FIG. 6 shows a structure similar to that of FIG. 5 but using the band electrodes of FIG. 2 and having complete circumferential gaps in the inner tubular member exposing the entire inner surfaces of the band electrodes.

FIG. 6 illustrates an alternative to the embodiment shown in FIG. 5. In FIG. 6 tip portion 10d includes an outer tubular member 38d similar to tip portion 10 of FIG. 2 and an inner tubular member 40d similar to inner tubular member 40 of FIG. 5. However, inner tubular member 40d has circumferentially extending cutouts 44 aligned with each band electrode 18 to permit all or a substantial part of inside surface 28 to be contacted by cooling saline 32, as opposed to the situation of FIG. 5 in which only a portion of the inside surface 28 is directly exposed to the cooling saline 32.

Tip portion 10 can be made by mounting or forming band electrodes 18 on a mandrel, and then filling the region between the lateral edges 26 of the band electrodes with a suitable polymer to create the tubular structure illustrated in FIG. 2. After curing, tip portion 10 is mounted to the distal-most polymer section 24 in a conventional manner, typically through the use of an adhesive or heat welding.

The construction of tip portion 10c could proceed generally as follows. A tubular member 40 is formed with holes 42 and then mounted on a mandrel. Spiral electrode 36 is then wound about inner tubular member 40 covering holes 42. A suitable thermoplastic polymer or thermoset material, such as silicone, is then introduced between opposed lateral sides 26b of spiral electrode 36 so to fill the space between the sides. When sufficiently cured, the structure is then removed from the mandrel and a tip electrode 20 can be mounted in a conventional fashion.

The above embodiments have been described on the basis that tip portion 10 has an exit opening 33 adjacent tip portion 10; see FIG. 1. This type of fluid flow, in which the cooling fluid, typically saline, exit adjacent or through the tip portion, is shown in U.S. Pat. No. 5,348,554, entitled "Catheter for RF Ablation with Cooled Electrode", and U.S. Pat. No. 5,462,521, entitled "Fluid Cooled and Perfused Tip for a Catheter", the disclosures of which are incorporated by reference. U.S. Pat. No. 5,348,554 also illustrates a catheter having a cooling fluid return passageway so that cooling fluid, after reaching the distal end of the tip section of the catheter, can be returned to the source so that the cooling fluid does not flow into the body but rather recirculates. Parallel conduit, recirculating systems can be used with the present invention. A system could also be devised in which part of the cooling fluid was directed out of the tip portion of the catheter shaft and part recirculated; fluid could also be directed out of the catheter at or between each electrode.

In use, tip portion 10 is located at the appropriate target site using manipulators 12 on handle 4. When in position, appropriate energy is applied to the ablation electrodes, such as band electrodes 18 or spiral electrodes 36, to ablate the tissue. During ablation, coolant, typically saline 32, is passed through port 21, through catheter shaft 6 and into interior 30 of tip portion 10 where the saline comes into direct physical contact with inner surface 28 of the ablation electrodes so to cool the ablation electrodes. This helps to reduce overheating in the vicinity of ablation electrodes 18, 36 thus helping to eliminate undesirable consequences of overheating, such as the excessive coagulation of blood and the unintended destruction of healthy tissue adjacent to the target site. The efficient cooling of the linear ablation electrode permits longer lesions to be created by permitting higher RF powers without resulting in excessive electrode heating. The lesions will be deeper into the tissue and will tend to flow into one another, that is join up, to create a linear lesion when using spaced-apart band or spiral electrodes. Cooling fluid, such as saline 32, can also be permitted to pass out of tip portion, such as through opening 33 adjacent to tip 20, or through other openings formed, for example, adjacent or through each band electrode 18; alternatively, some or all of the cooling fluid could be caused to recirculate and not be expulsed from tip portion 10.

It is known to cool a tip electrode and apply the cooled tip electrode to a target site while monitoring the heart to see if cooling the target site has a positive affect on arrhythmia; if it does then the tissue at the target site is ablated. The invention can also be used to test for the expected effectiveness of creating a linear lesion at a target site. To do so tip portion is positioned so the linear ablation electrode is at the target site and the linear electrode is cooled by the cooling fluid to chill the tissue sufficiently to create what is sometimes called a test lesion. If chilling the tissue at the target site affects arrhythmia in a positive way, energy is supplied to the linear ablation electrode to ablate the tissue and create a linear lesion at the target site.

Figure 7:
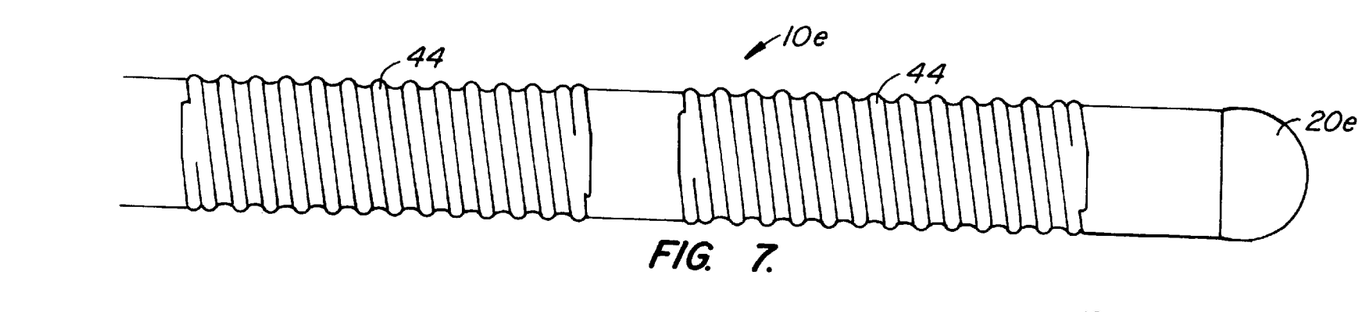
FIG. 7 illustrates an alternative tip portion showing two spiral electrodes having circular cross-sectional shapes embedded within an outer tubular member, the inside surface of the electrodes and the outer tubular member being covered by a porous liner.
Figures 7A, 7B, 7C, 8:
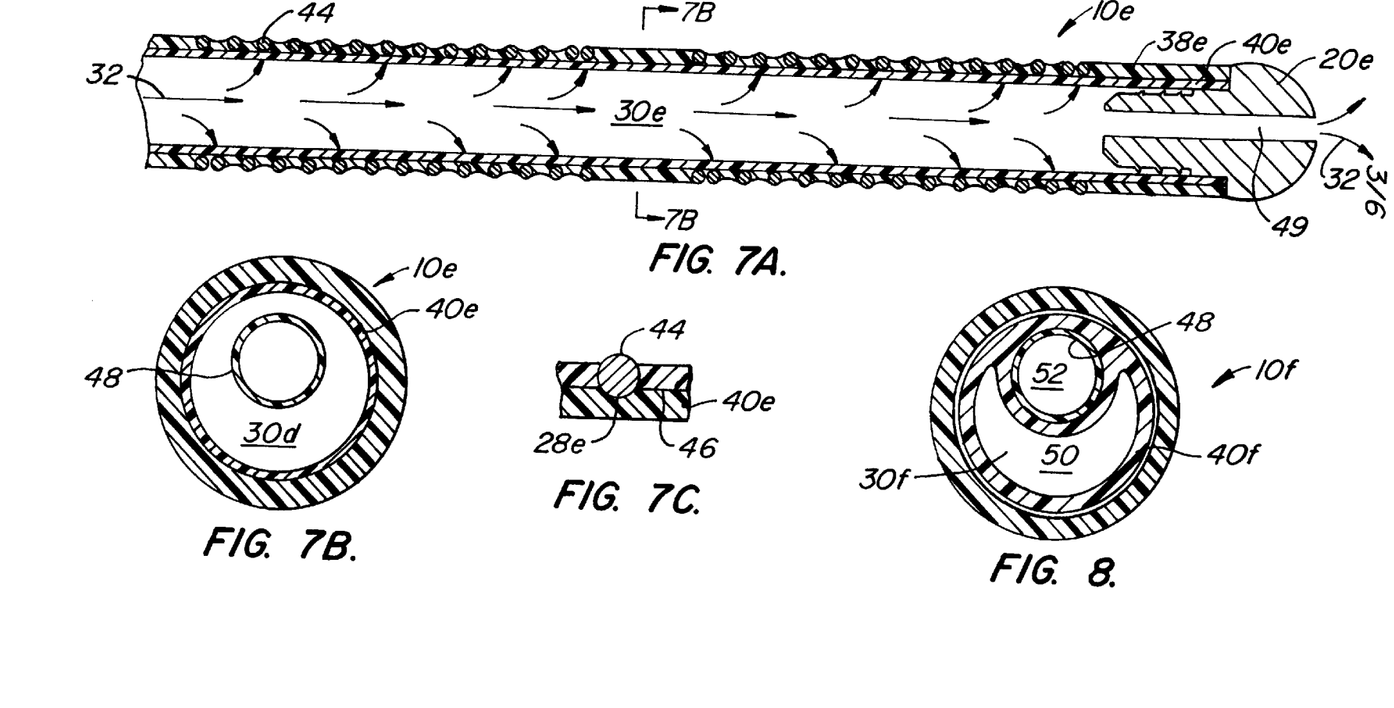
FIG. 7A is a longitudinal cross-sectional view of the tip portion of FIG. 7.
FIG. 7B is a radial cross-sectional view taken along line 7B—7B of FIG. 7 showing an inner fluid flow passage defined within the interior of the tip portion and a fluid impermeable tube also within the interior and through which various electrical wires and manipulator elements can pass, the tube not being shown in FIG. 7A for ease of illustration.
FIG. 7C is an enlarged view of a portion of FIG. 7A illustrating the exposure of the inside surface of the spiral electrode to the porous liner.
FIG. 8 is a view similar to FIG. 7B but showing a porous bi-lumen extrusion within the interior of the tip portion.

FIGS. 7–7C illustrate alternative tip portion 10e comprising a plurality of spiral electrodes 44 having circular cross-sectional shapes. Electrodes 44 are embedded within and carried by outer tubular member 38e. The inside surfaces 28e, see FIG. 7C, of spiral electrodes 44 and the inside surface 46 of outer tubular member 38e are covered by a porous inner tubular member 40e.

Porous inner tubular member 40e is preferably a silicone, polyolefin, or other suitable porous material about 0.001"–0.010" thick, more preferably about 0.003"–0.008" thick, to provide fluid access to the inner surface 28e of electrodes 44 while providing some structural support to tip portion 10e. FIG. 7B illustrates a liquid impervious tube 48 extending along the interior 30e of tip portion 10e. Tube 48 is used to guide various wires and other components along tip portion 10e and keep those components from being exposed to cooling fluid 32. In the embodiment of FIGS. 7–7C cooling fluid 32 exits tip portion 10e through an axial hole 49 formed in tip portion 10e. Alternatively, an additional tube, similar to tube 48, could be used to direct cooling fluid 32 in a reverse fluid flow along tip portion 10e.

FIG. 8 illustrates a cross-sectional view similar to that of FIG. 7B but using a porous bi-lumen extrusion as the inner tubular member 40f. Inner tubular member 40f divides interior 30f into a main region 50, through which cooling fluid 32 flows, and a supplemental region 52 housing tube 48, tube 48 serving the same purpose as in the embodiment of FIGS. 7–7C. Extrusion 40f may be made of a suitable porous material such as polyethylene, polyolefin or silicone.

Figure 9:
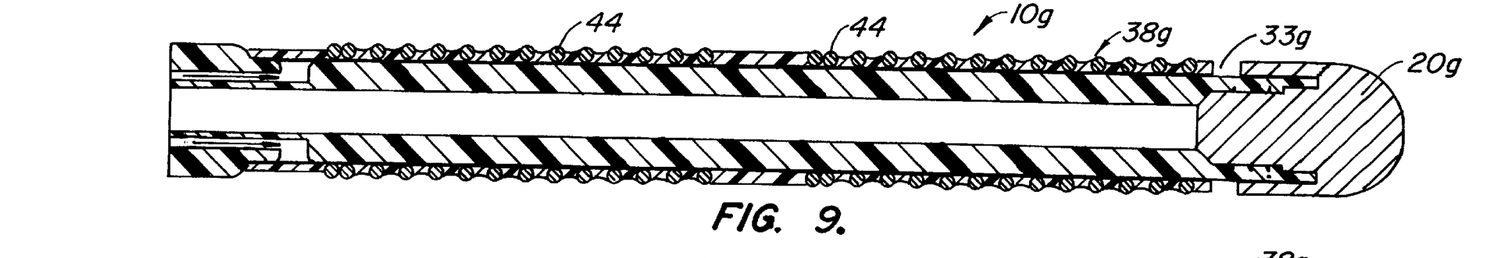
FIG. 9 is a longitudinal cross-sectional view of an alternative tip portion made according to the invention.
Figure 9A:
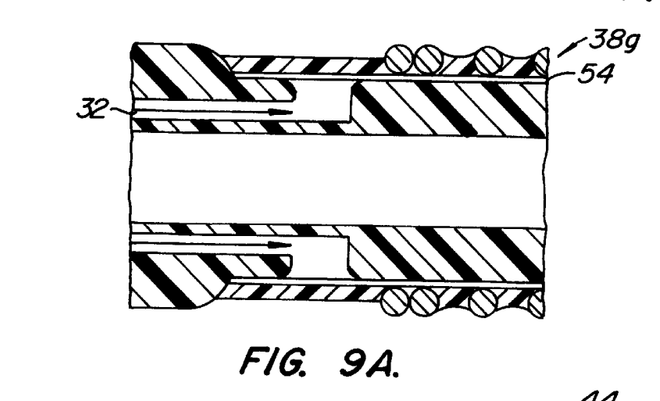
FIG. 9A is an enlarged view of a portion of the tip portion of FIG. 9 showing the entrance to the fluid passage.
Figure 9B:
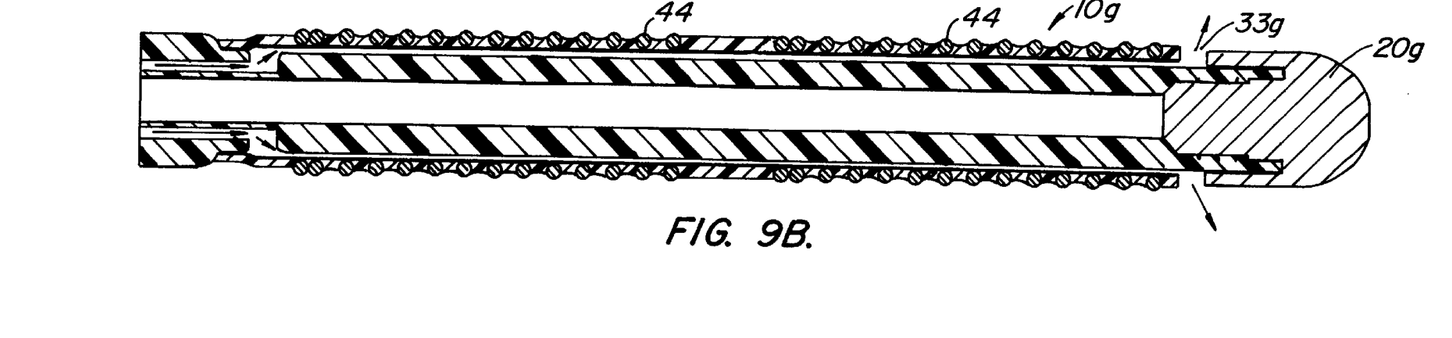
FIG. 9B illustrates the tip portion of FIG. 9 during fluid flow through the fluid passage.
Figure 9C:
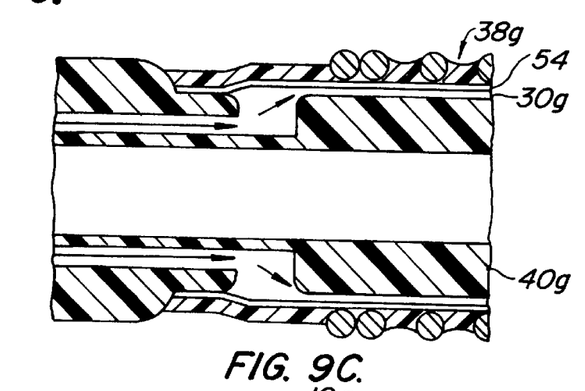
FIG. 9C is an enlarged view of a portion of the tip portion of FIG. 9B illustrating passage of the cooling fluid into the fluid passage.

FIGS. 9–9C illustrate a further embodiment of the invention in which a tip portion 10g has a radially expandable outer tubular member 38g. Member 38g includes a silicone layer 54 which dilates to define fluid passage 30g, see FIG. 9C, between silicone layer 54 and inner tubular member 40g. This dilation occurs when cooling fluid 32 is supplied at a sufficiently high pressure at the entrance 56 to fluid passage 30g to cause the cooling fluid to flow along the dilated passage 30g and exit tip portion 10g at exit openings 33g. Silicone layer 54 is sufficiently thin, such as 0.0005" to 0.002" thick, so that cooling fluid 32 need not actually contact the inside surfaces of electrodes 44 to effectively cool the electrodes. Alternatively, silicone layer 54 can be a porous silicone to provide actual direct contact of the cooling fluid with the inside surfaces of electrodes 44.

Figure 10:
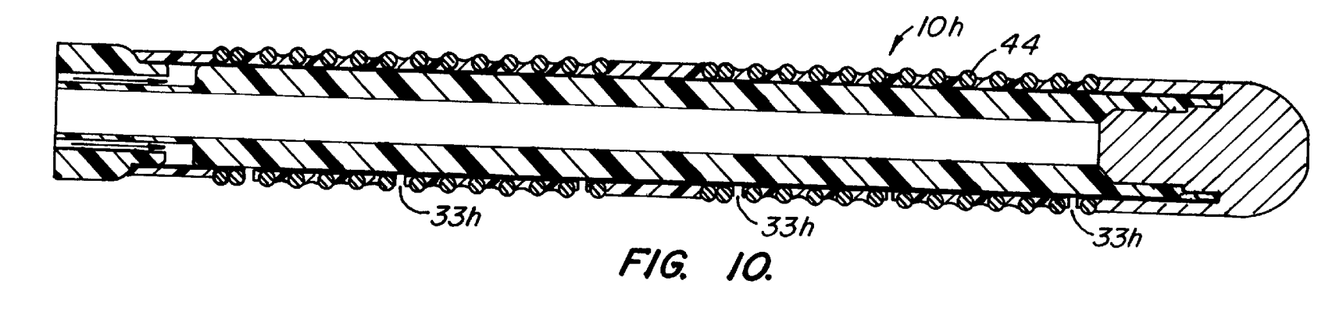
FIG. 10 is a view similar to FIG. 9 of an alternative embodiment in which several exits from the fluid passage are positioned along the length of the tip portion.

FIG. 10 illustrates a tip portion 10h similar to tip portion 10g but having a number of exits 33h along the tip portion. This can be useful because it not only causes convective cooling of the electrodes, but causes the cooling fluid to also directly cool or "bathe" the issue being ablated.

Figure 11:
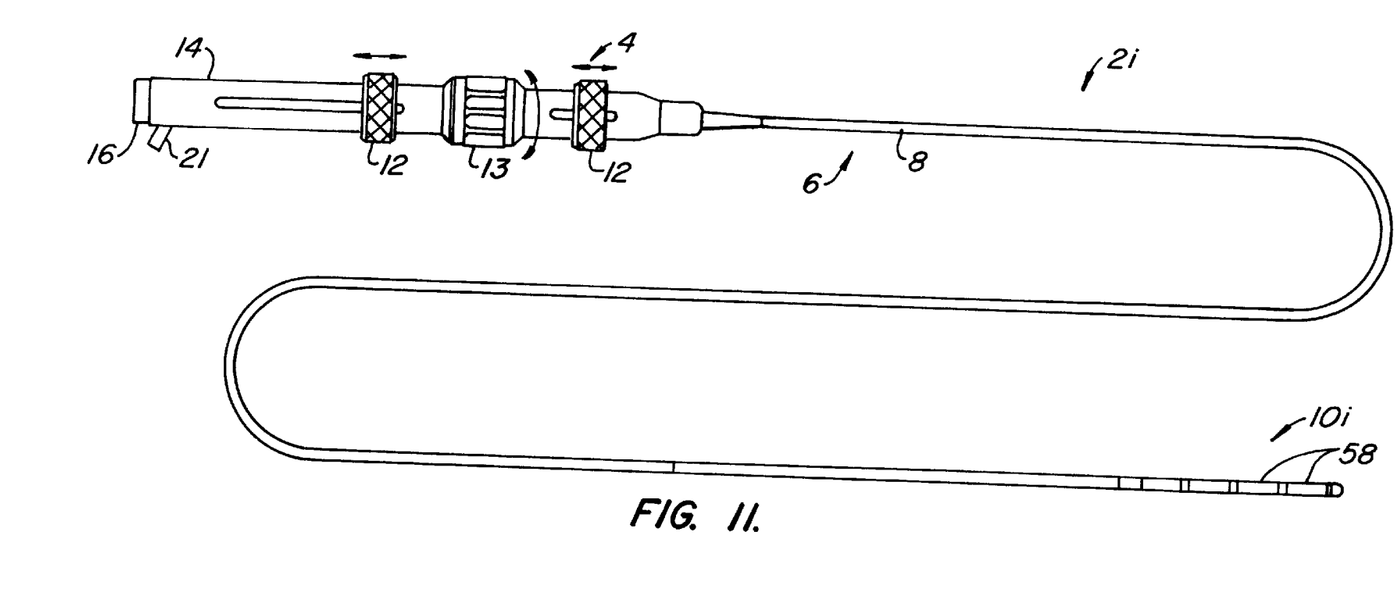
FIG. 11 is an overall view of a further embodiment of a catheter assembly using hollow spiral electrodes.
Figure 11A:
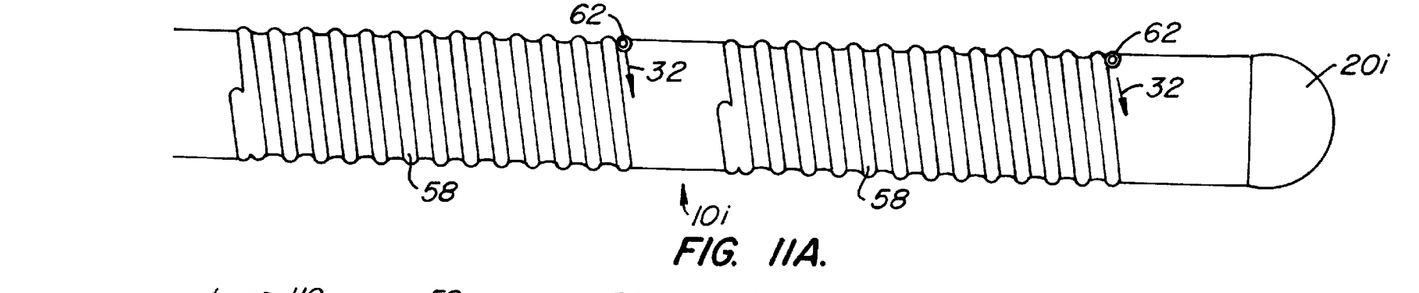
FIG. 11A is an enlarged view of a part of a tip portion of the catheter assembly of FIG. 11.
Figure 11B:
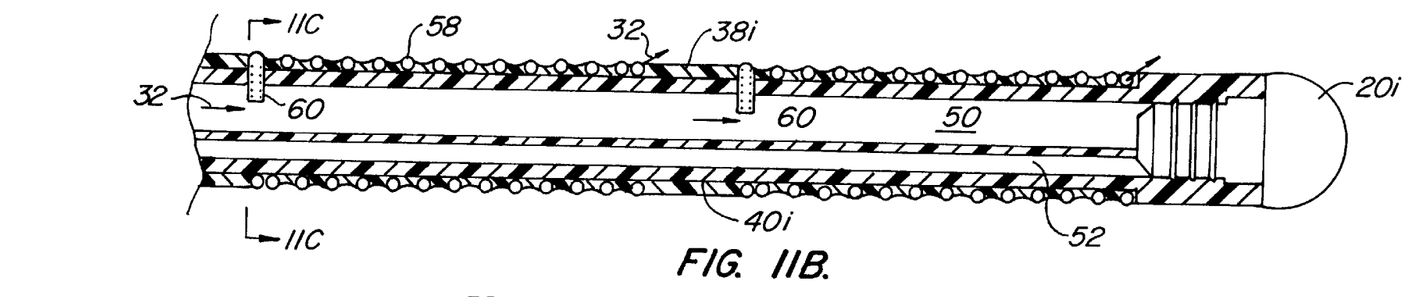
FIG. 11B is a longitudinal cross-sectional view of the tip portion of FIG. 11A illustrating the flow of cooling fluid through the spiral electrodes.
Figure 11C:
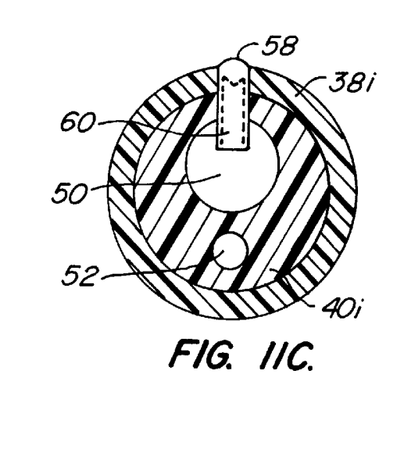
FIG. 11C is a cross-sectional view taken along line 11C—11C of FIG. 11B.
Figure 12:
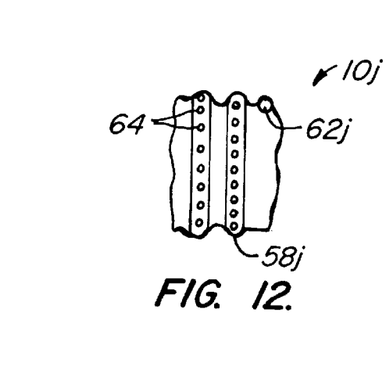
FIG. 12 is a partial side view of the tip portion of a still further embodiment of the invention.

FIGS. 11–11C illustrate a further embodiment of the invention in which a tip portion 10i has a plurality of tubular spiral electrodes 58. Electrodes 58 are preferably stainless steel hypotubes having an outside diameter of about 0.014" and an inside diameter of about 0.010". Proximal end 60 of each tubular electrode 58 opens into region 50 defined within inner tubular member 40h and through which cooling fluid 32 flows. Cooling fluid flows into proximal end 60, through the interior of tubular spiral electrode 58 and out through the distal end 62 of the spiral electrode. In this embodiment the inside surface of spiral electrode 58 corresponds to inside surface 28 of the electrodes in the other embodiments and permits direct cooling contact of the cooling fluid with the electrode. Although in this embodiment each electrode 58 has a single entrance and a single exit, each spiral electrode could have one or more entrances and one or more exits. For example, distal ends 62 could be blocked and spiral electrodes 58 could have numerous small openings 64, see FIG. 12, through which cooling fluid could flow out of tip portion 10j. The sizes of the small openings could be chosen to ensure generally equal or unequal flow rates through the openings.

Other modifications and variation can be made to the disclosed embodiments without departing from the subject of the invention as defined in the following claims. For example, the invention could be constructed to ablate other than cardiac tissue, such as the prostate, the uterus, cancer tumors, or coronary artery blockages (plaques). Temperature sensors may be used to measure the temperature at the tissue interface; to do so temperature sensors should be positioned to provide the most accurate temperature measurements, typically positioned spaced-apart from the fluid-cooled electrodes. To increase the ID/OD ratio for the hollow coil design of FIGS. 7–12, the hollow coil could have a flattened, rather than circular, cross-sectional shape. This smaller profile electrode would allow a smaller shaft OD or a larger shaft ID for catheter shaft components, such as fluid lumen, manipulator wire(s), electrical wires, etc.

What is claimed is:

1. An ablation catheter assembly comprising:
    a handle;
    a catheter shaft extending from the handle;
    the catheter shaft comprising a tip portion with a fluid passage and a distal end;
    at least one spiral tubular ablation electrode circumscribing the tip portion;
    the at least one spiral tubular ablation electrode having a fluid entrance and a fluid exit and defining a fluid flow path therebetween; and
    said fluid entrance fluidly coupled to said fluid passage so that a fluid passing through said fluid passage can enter and flow through said at least one spiral tubular electrode in a spiral path.

2. The catheter according to claim 1 wherein said fluid passage has a cooling fluid entrance to provide a cooling fluid to said passage and into said at least one spiral tubular electrode.

3. The catheter according to claim 1 wherein said at least one spiral tubular ablation electrode comprises a plurality of spaced-apart tubular spiral electrodes.

4. The catheter according to claim 1 wherein said at least one spiral tubular ablation electrode has a circular cross-sectional shape.

5. The catheter according to claim 1 wherein said at least one spiral tubular ablation electrode is spaced apart from the distal end.

6. The catheter according to claim 1 wherein said fluid exit opens into a region external of said catheter shaft.

7. The catheter according to claim 1 wherein said at least one spiral tubular ablation electrode comprises a plurality of said fluid exits.

8. The catheter according to claim 1 wherein said at least one spiral tubular ablation electrode comprises one said fluid entrance.

9. The catheter according to claim 1 wherein said at least one spiral tubular ablation electrode comprises one said fluid exit.

10. An ablation catheter assembly comprising:
    a handle;
    a catheter shaft extending from the handle;
    the catheter shaft comprising a tip portion with a fluid passage and a distal end;
    the tip portion further comprising at least one linear ablation electrode spaced-apart from the distal end;
    said at least one linear ablation electrode comprising outer and inner surfaces;
    said inner surface being effectively fluidly exposed to said fluid passage so that a cooling fluid passing through said fluid passage effectively directly contacts said inner surface to cool the at least one linear ablation electrode; and
    said tip portion comprising inner and outer tubular members defining said fluid passage therebetween, said fluid passage comprising an entrance, an exit, and a pressure-sensitive portion which opens only when the fluid pressure at the entrance of said fluid passage exceeds a chosen level so the cooling fluid can pass along the fluid passage from the entrance to the exit.

11. The catheter according to claim 10 wherein said at least one linear ablation electrode comprises a plurality of spaced-apart band electrodes.

12. The catheter according to claim 11 wherein at least one of said band electrodes is circular.

13. The catheter according to claim 11 wherein at least one of said band electrodes is semicircular.

14. The catheter according to claim 10 wherein said at least one linear ablation electrode comprises a plurality of spiral electrode.

15. The catheter according to claim 10 wherein said entire inner surface of said at least one linear ablation electrode is exposed to said fluid passage.

16. The catheter according to claim 10 wherein at least portions of said inner surface of said electrode are exposed to said fluid passage.

17. The catheter according to claim 10 further comprising a liquid permeable porous material covering said inner surface.

18. The catheter according to claim 10 wherein the inner surface is a bare surface exposed directly to said fluid passage.

19. The catheter according to claim 10 wherein the fluid passage comprises a plurality of said exits.

20. A method for cooling at least one spiral ablation electrode of an ablation catheter assembly comprising:
    positioning a tip portion of a catheter shaft of an ablation catheter assembly at a target site of a body organ;
    flowing cooling fluid through said at least one spiral tubular ablation electrode along a spiral path thereby cooling said at least one spiral tubular ablation electrode;
    whereby an improved lesion can be created by said ablation catheter assembly due to the efficient cooling of the tubular ablation electrode, thereby allowing energy to be delivered by the electrode at a higher power levels for a longer duration.

21. The method according to claim 20 whereby said at least one spiral tubular ablation electrode creates a plurality of lesions which join one another to form said improved lesion.

22. The method according to claim 20 wherein said positioning step is carried out with the target site being within a heart of a patient.

23. The method according to claim 20 wherein said flowing step is carried out using chilled saline as the cooling fluid.

24. The method according to claim 20 wherein the flowing step is carried out using at least one spiral tubular ablation electrode which is spaced apart from the distal end of the tip portion.

25. The method according to claim 20 wherein said flowing step is carried out by flowing cooling fluid through a plurality of spiral tubular ablation electrodes.

26. The method according to claim 20 wherein said flowing step is carried out by flowing cooling fluid through a perforated spiral tubular ablation electrode.

* * * * *